Figure 3:
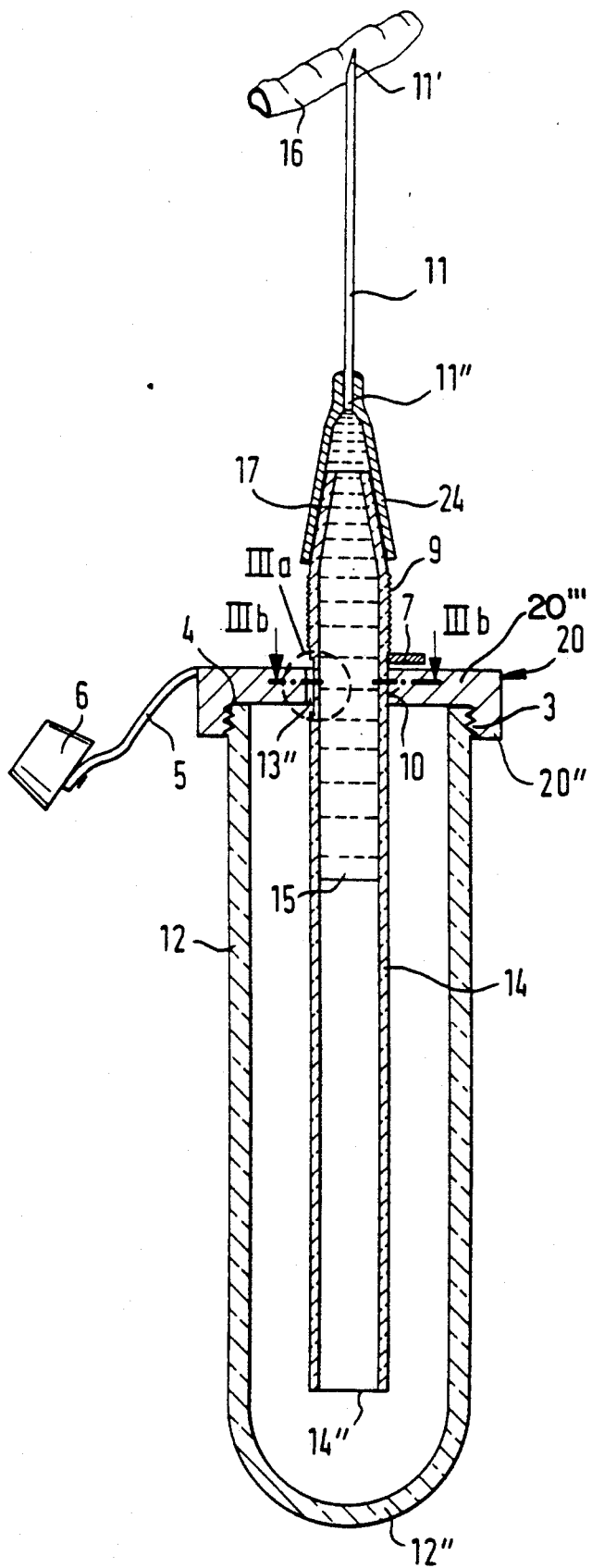

United States Patent [19]

Sarstedt

[11] Patent Number: 5,165,419
[45] Date of Patent: Nov. 24, 1992

[54] BLOOD EXTRACTION DEVICE

[75] Inventor: Walter Sarstedt, Nuembrecht-Rommelsdorf, Fed. Rep. of Germany

[73] Assignee: Walter Sarstedt Geraete und Verbrauchsmaterial fuer Medizin und Wissenschaft, Nuembrecht-Rommelsdorf, Fed. Rep. of Germany

[21] Appl. No.: 587,182

[22] Filed: Sep. 24, 1990

[30] Foreign Application Priority Data

Sep. 26, 1989 [DE] Fed. Rep. of Germany ....... 3932112

[51] Int. Cl.⁵ ............................................... A61B 5/00
[52] U.S. Cl. ..................................... 128/763; 128/760
[58] Field of Search ............... 128/763, 770, 766, 760, 128/762, 765; 604/21, 187, 240, 207, 218, 232, 235, 239; 73/864.01, 864.02

[56] References Cited

U.S. PATENT DOCUMENTS

| 2,727,517 | 12/1955 | Wilkin | 128/763 |
| 3,063,451 | 11/1962 | Kowalk | 128/763 |
| 4,298,011 | 11/1981 | Mangurten et al. | 128/763 |
| 4,411,163 | 10/1983 | White | 128/763 |
| 4,900,515 | 2/1990 | Miramanda | 73/864.02 |

FOREIGN PATENT DOCUMENTS 7901131 12/1979 United Kingdom ............ 73/864.02

Primary Examiner—Max Hindenburg
Assistant Examiner—Guy V. Tucker
Attorney, Agent, or Firm—Townsend and Townsend

[57] ABSTRACT

A blood extraction device has a cannula (11) the front end of which can be stuck into the vein of a patient and the rear end (11″) of which stands in flow communication with the interior of a sample tubule (12) which is hermetically closed at its rear end (12″) and is closed at its front end, apart from an air vent (13, 13′). An inner tube (14) extending into the interior of the sample tubule (12) sealingly adjoins the rear end (11′) of the cannula (11) and has an internal cross-section such that during the taking of blood a continuous blood column (15) is pressed from the rear end (11″) of the cannula (11) into the internal tube (14) and does not break away in any position of the sample tubule (12) relative to the direction of gravity, i.e. even when the tubule is arranged beneath the cannula (12), at least so long as the cannula (11) is inserted in the vein (16).

17 Claims, 2 Drawing Sheets

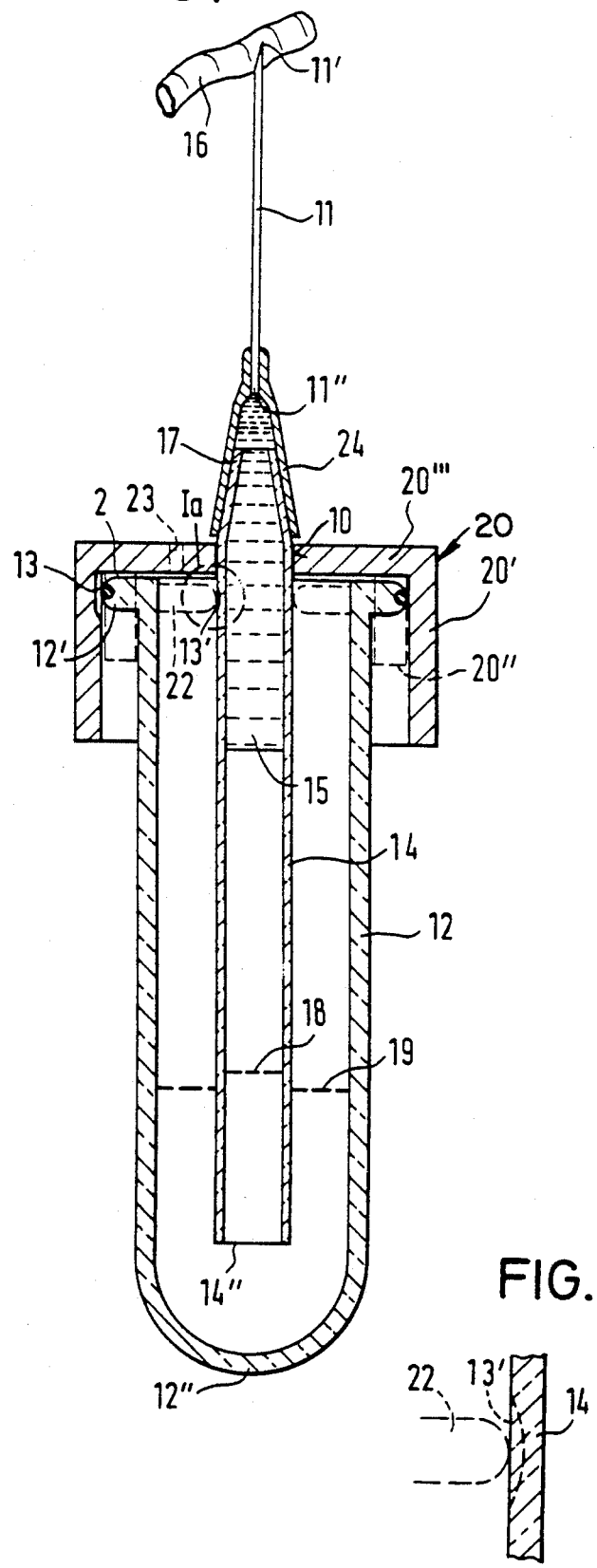
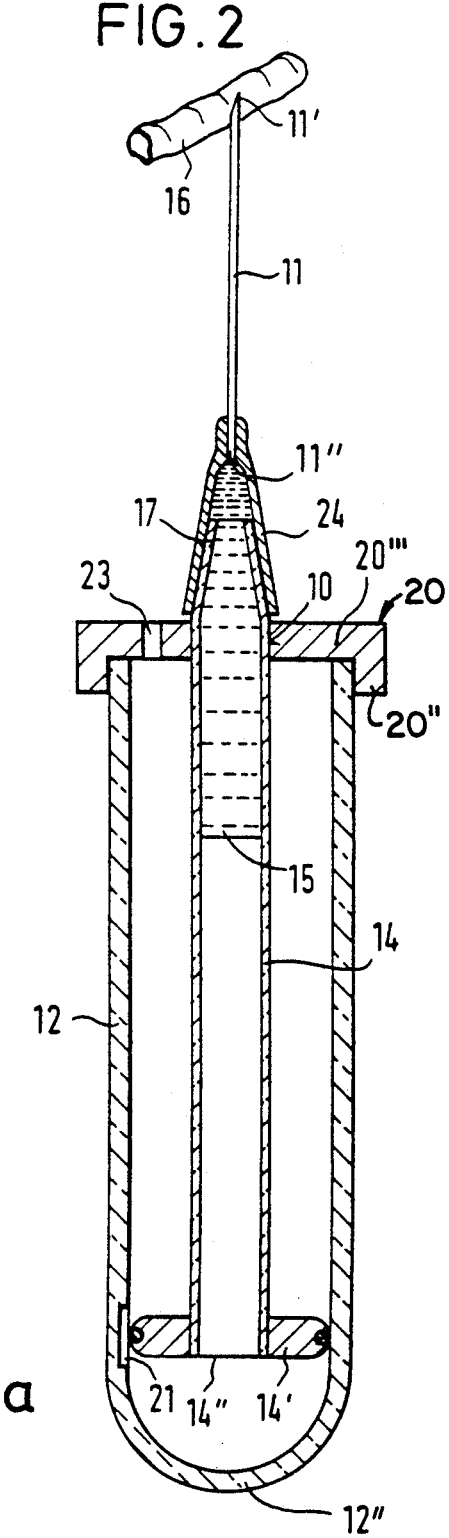

BLOOD EXTRACTION DEVICE

The invention relates to a blood extraction device comprising a cannula, the front end of which can be inserted into the vein of a patient and the rear end of which is in flow communication with the interior of the sample tubule, which is hermetically sealed at its rear end and is closed at its front end apart from an air vent.

Blood extraction devices which operate without pistons and vacuum are already known for the extraction of the smallest quantities of blood (DE-PS 27 51 503). These devices operate on the basis of the capillary effect and can pick up the blood emerging from a puncture wound in the finger tip or ear lobe of the patient and collect it in a sample tubule. A disadvantage of these blood extraction devices is the fact that they must operate with blood which emerges from a puncture wound which is contaminated with tissue fluid and which can also be mixed with microbes or contamination present on the skin, so that a troublefree blood sample which corresponds to venous blood is not present. This kind of blood extraction is also not particularly hygienic because the skin and eventually also the patient's clothing can be contaminated with the blood which emerges from the wound.

For this reason there have been blood extraction devices in which the rear end of a cannula opens into a sample tubule which receives the blood and the cannula can be inserted into, i.e. puncture, a vein of a patient. The blood pressure then presses the blood automatically through the cannula into the sample tubule where it is collected and, after the sample tubule has been adequately filled, the latter can be passed on for further use. Venous blood in faultless form can be obtained with such blood extraction devices and is in no way contaminated by microbes or other foreign bodies.

A disadvantage of these known blood extraction devices is however the fact that venting bores and passages must be provided in the cover of the sample tubule which have to be kept free of blood. In this way the manipulations which can be undertaken with the known device are restricted to the extent that the sample tubule should always be held with its rear end or base more or less at the bottom, so that the blood which has entered into the sample tubule through the cannula cannot reach the vent openings and emerge there. It is also disadvantageous that with the cannula held more or less downwardly the filling procedure for the sample tube is difficult to observe.

The object of the invention lies in providing a blood extraction device of the initially named kind in which the sample tubule and the cannula can be held in any desired position during the taking of blood, without the danger of blood emerging into the air vent passages and openings which are generally provided in the front end of the sample tubule, with it moreover being possible to precisely observe the filling process and to interrupt the extraction of blood after attaining the desired degree of filling.

In order to satisfy this object the invention provides that an inner tube extending into the interior of the sample tubule sealingly adjoins the rear end of the cannula and has an internal cross-section such that, on the one hand, the largest possible internal volume is present which makes it possible to timely interrupt the filling process and, on the other hand, such that during the taking of blood a continuous blood column is pressed from the rear end of the cannula into the internal tube and does not break away in any position of the sample tubule relative to the direction of gravity, i.e. even when the tubule is arranged beneath the cannula, at least so long as the cannula is inserted in the vein, i.e. not even when the cannula points vertically upwardly.

The inner tube and the sample tubule should be at least translucent and preferably transparent.

The concept underlying the invention is thus to be seen in the fact that the sample tubule is not filled directly with the blood pushed into the cannula but rather that an inner tube which is preferably easily visible from the outside is first filled with blood. Since the inner tube is expediently transparent its gradual filling can be straightforwardly observed from the outside and thus the extraction of blood can be terminated after reaching the predetermined degree of filling. Only after this is the blood introduced in a second phase from the inner tube into the sample tubule, in which it can then be investigated or treated in any desired manner, for example by centrifuging or through despatch to a laboratory.

For the dimensioning of the inner tube it is, on the one hand, important that the largest possible volume can be taken up because the quantity of blood which can as a whole be picked up by the blood extraction device is restricted by the inner volume of the inner tube. On the other hand, the inner tube may not have a cross-section which is so large that, for example with an upwardly directed cannula and a downwardly directed sample tubule, the blood column which has entered into the inner tube from the top during the taking of blood breaks away and thus the blood prematurely passes into the sample tubule, i.e. before termination of the blood extraction. The inner tube thus has a substantially larger cross-section than a capillary, however the capillary forces are still sufficiently large to ensure that the blood column holds together in any position of the inner tube.

The inner tube preferably has circular cross-section and extends coaxial to the sample tubule which is likewise preferably of right-cylindrical shape.

It is particularly advantageous when the inner tube and the cannula are arranged on a cover which is mounted on the front end of the sample tubule. With this arrangement the construction should in particular be such that the air vent is provided in the cover or between the cover and the sample tubule or between the inner tube and the cover.

In this embodiment the cover with the inner tube can be removed during or after transfer of the blood from the inner tube into the sample tube, so that finally only the sample tube is present which is filled in the desired manner with blood and which can then be closed by a plug or can also be handled in other ways for investigatory purposes.

In so far as the blood is to be removed by gravity from the inner tube after termination of the blood extraction, an advantageous embodiment of the invention provides that the inner tube has an internal cross-section which is of a size such that when the cannula is withdrawn from the vein, or is removed from the front end of the inner tube, and when the blood sample tube is upright, the blood column which has collected in the inner tube automatically emerges downwardly into the sample tubule.

In order with this embodiment to prevent contamination of the inner tube with the blood transferred into the sample tubule provision is made in accordance with a further advantageous embodiment that the inner tube only projects sufficiently far into the sample tubule that, after the running out of the blood column into the sample tubule, the blood level in the sample tubule is located beneath the lower end of the inner tube.

It is however particularly advantageous when, after the filling of the inner tube with the blood column, a partial vacuum can be generated in the interior of the sample tubule by means of which the blood column is sucked out of the inner tube into the sample tubule.

In this way the blood column which is located in the inner tube is necessarily sucked out by the partial vacuum. Although the blood could also be sucked out of capillary-like inner tubes it is preferred, in accordance with the invention, to provide the inner tube with a cross-section which lies substantially above the cross-section of a capillary, so that the largest possible volume of blood can be picked up by the inner tube.

When the inner tube is fixedly arranged in the cover a first advantageous arrangement for generating a partial vacuum after the extraction of blood is characterised in that the cover, which preferably has a collar acting as a cylinder, cooperates in the manner of a piston-in-cylinder arrangement with the sample tubule, which preferably has a peripheral bead which acts as a piston, with at least one vent passage being provided in the inner wall of the collar and only bridging the sealing surface of the peripheral bead in the blood extraction position.

In accordance with a further advantageous embodiment provision can also be made, for the same purpose, that a piston is preferably arranged at the rear end of the inner tube and is in sealing contact with the inner wall of the sample tubule, with at least one vent passage which only bridges the sealing surface of the piston in the blood extraction position being provided in the inner wall of the sample tubule.

Finally, the partial vacuum can also be generated in simple manner in that a ring piston is preferably arranged at the front end of the sample tubule at the inside and is in sealing connection with the outer wall of the inner tube, with a vent passage being provided in the outer wall of the inner tube and only bridging the inner sealing surface of the ring piston in the blood extraction position.

The inner tube is advantageously axially displaceable in the cover, i.e. can be drawn out of the cover bore in piston-like manner so that by pulling the inner tube out of the cover the partial vacuum can be generated which empties tube. In this case provision should be made that in the state in which the inner tube is pushed into the greatest degree the inner tube projects sufficiently far outwardly beyond the cover that it can readily be grasped there, in particular at a knurled surface or friction surface provided there.

In order that a problem-free venting of the inner space of the sample tubule is possible during blood extraction, a preferred embodiment provides that a vent passage is provided in the wall of the inner tube thereby connecting the atmosphere and the region directly beneath the cover with one another, in the state of the inner tube in which it is pushed inwardly to the greatest degree. The vent passage being closed for the generation of a partial vacuum even when the inner tube has been pulled out to a small degree, whereupon a sealed sliding connection is present between the inner tube and the cover.

The air vent can be particularly simply ensured when the vent passage is formed by a partial flattening of the inner tube which extends fractionally above and/or below the cover in the state in which the inner tube is pushed in to the greatest degree.

In order to ensure unhindered emergence of the blood from the inner tube into the sample tubule, provision should further be made in accordance with the invention that, in the state in which the inner tube is pushed in to the greatest degree, it still does not touch the base of the sample tubule.

In order to clearly define the position of the inner tube in which it is pushed inwardly to the greatest degree a further embodiment is so formed that an abutment on the part of the inner tube which projects out of the cover determines the position of the inner tube in which it is pushed inwardly to the greatest degree.

In order that the opening which remains in the cover can be sealingly closed after extraction of the inner tube, a plug should be provided for closing the cover bore and is expediently attached to the cover via a flexible band so that it cannot be lost.

Figure 3A:
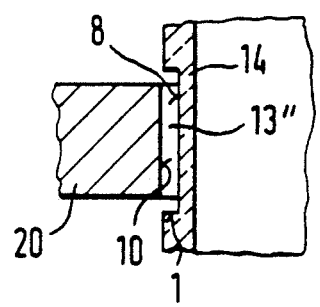
Figure 3B:
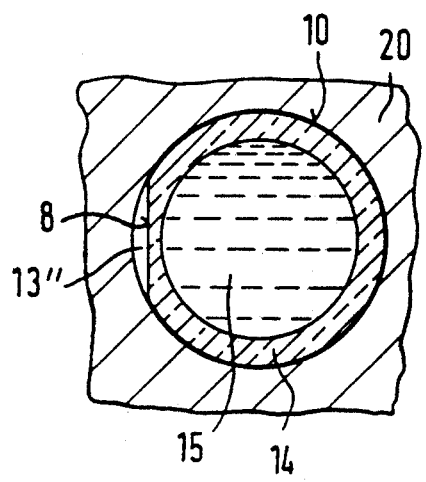

The invention will be described in the following by way of example and with reference to the drawings in which are shown:

FIG. 1 a partially sectioned schematic side view of first embodiment of a blood extraction device in accordance with the invention, FIG. 1a the detail Ia of FIG. 1 to a larger scale, FIG. 2 a corresponding partially sectioned schematic side view of a further embodiment, FIG. 3 a partially sectioned side view of a third embodiment, FIG. 3a the detail IIIa of FIG. 3 to an enlarged scale, and FIG. 3b a section on the line IIIb—IIIb in FIG. 3.

As seen in FIG. 1 the front end 11' of a cannula 11 is located within a schematically illustrated vein 16 of a patient. The rear end region of the cannula 11 extends through a mounting cone 24 which is sealingly pushed onto a mounting cone 17 formed at the front end of an inner tube 14. The rear end 11'' of the cannula opens flush with the interior of the mounting cone 24.

The inner tube 14 extends through a central bore 10 in a cover 20 into the interior of a sample tubule 12 which is closed at the top by the cover 20 and is closed at the bottom by a rounded base 12''. In order to provide the largest possible internal volume the inner tube 14 preferably extends down to the region of the base 12'' of the sample tubule 12. The front or upper end of the sample tubule 12 has peripheral bead 12' which, in the manner of a piston, cooperates with a right-cylindrical collar 20' which is moulded onto the cover 20 radially at the outside and which extends rearwardly or downwardly. In the blood extracting position shown in FIG. 1 the cover 20 is in the blood extracting position in which it is fully mounted onto the sample tube 12 in which an axial vent passage 13 provided at the inside in the collar 20' bridges the peripheral sealing surface of the piston-like peripheral bead 12'. In this manner the interior of the sample tube 12 can be vented via the gap 2 between the cover 20 and the peripheral bead 12' and also via the vent passage 13. Suitable abutment means can be provided on the cover or sample tube to prevent undesired closure of the venting gap 2.

The manner of operation of the described blood extraction device is as follows:

As a result of the blood pressure present in the vein 16 the blood is pushed into the cannula 11 and from the latter through the mounting cone 17 into the inner tube 14 where a continuous blood column 15 is formed which does not break away or break up even in the vertical position of the cannula 11 shown in FIG. 1, since the cross-section of the inner tube 14 is made appropriately small. The cross-section should however, on the other hand, be made as large as possible so that the quantity of blood collected there is sufficient to fill the sample tubule 12 as far as possible in the later stadium of the filling process.

The blood extraction is preferably continued until the blood column 15 is located close to the rear or lower end 14" of the inner tube 14. The instant at which this degree of filling is achieved can be observed without problem in any desired position of the sample tubule 12 or of the cannula 11, since both the sample tubule 12 and also the inner tube 14 are transparent. After complete filling of the inner tube 14 the cannula 11 is extracted from the vein 16.

The cover 20 is now drawn away forwardly from the sample tubule 12. The vent passage 13, which is of correspondingly short axial length and which only extends a small amount beneath the peripheral bead 12', first closes and a vacuum is subsequently built up in the interior of the sample tubule 12 through the parts 12', 20' which cooperate in the manner of a piston-in-cylinder arrangement. The partial vacuum ensures that the blood column 15 is sucked out of the interior of the inner tube 14 into the surrounding sample tubule 12. In order to accelerate this process the cannula 11 can previously be removed from the mounting cone 17.

The length of the collar 20' is to be dimensioned in such a way that after it has moved out of engagement with the peripheral bead 12' the inner tube 14 is fully emptied into the sample tube 12.

Instead of providing the ring piston 14' at the lower end of the inner tube 14 an inner ring piston 22 can also be provided at the upper end of the sample tube 12 in the manner shown in broken lines in FIGS. 1 and 1a, with the inner ring piston 22 being in sealing connection with the outer surface of the inner tube 14, and with the collar 20" directly contacting the outer wall of the sample tube 12. A vent passage 13' corresponding to the passage 13 of the first embodiment is provided at the inner tube 14 between the cover 20 and the inner tube 14. The vent passage 13' ensures the venting to atmosphere only in the blood extraction position which can be seen from FIGS. 1 and 2, provided the vent bore 23 shown in broken lines or other cover vent is provided.

The ratio of the inner volume of the sample tube 14 to the inner volume of the sample tube 12 should be selected such that the blood column rises more slowly in the sample tube 12 than the rate at which the inner tube 14 is removed from the sample tubule 12, so that the outer side of the inner tube 14 does not become contaminated with blood when transferring the blood column 15 into the sample tubule 12. In this way no danger of contamination exists after complete removal of the inner tube 14 from the sample tube 12.

The apparatus of FIG. 1 can however also operate without the piston-in-cylinder arrangement 12', 20', with the vent passage 13 either extending axially up to the lower edge of the collar 20', or with a special vent opening 23 being provided in the cover 20. However, in this case, the cross-section of the inner tube 14 must be sufficiently large that after extraction of the cannula 11 from the vein 16, or at least after removal of the cannula 11 from the mounting cone 17, the blood column 15 automatically runs downwardly into the sample tubule 12 by gravity in the upright position of the sample tubule 12 shown in FIG. 1. In order, in this case, to also avoid contamination of the outer side of the inner tube 14 with blood, the lower end of the inner tube 14 should be removed somewhat further from the lower end 12" of the sample tubule 12. It should for example lie at the position 18 shown in broken lines in FIG. 1. The blood of the blood column 15 which flows into the sample tube 12 by gravity would then only rise to the level 19 which is likewise shown in broken lines in FIG. 1.

In accordance with FIG. 2, in which the same reference numerals are used to designate parts which correspond to parts of FIG. 1, a ring piston 14' is provided at the lower end of the inner tube 14 in order to generate a partial vacuum after blood extraction. The ring piston 14' consists of plastic with a seal set into the periphery, or with sealing lips provided there, and is thus in sealing connection with the inner wall of the sample tube 12. In the blood extracting position which is evident from FIG. 2, in which the inner tube 14 is located in its lowermost or rearwardmost position, an axial vent passage 21 bridges the peripheral sealing surface of the ring piston 14 so that the air displaced during rising of the blood column 15 can escape into the above lying space, and can finally escape through the vent bore 23 in the cover 20. In accordance with an advantageous modification the diameter of the inner tube 14 is so large that the piston 14' can be formed by an O-ring which is laid into a peripheral groove of the inner tube 14 and which contacts the inner wall of the sample tubule 12. It is also possible to fixedly connect the inner tube 14 with the cover 20, in particular to make it in one piece therewith. These parts can then be formed as an injection moulding onto which it is then only necessary to mount an O-ring, which can in particular be snapped into place.

The cover 20 is removably sealingly mounted onto the front end of the sample tubule 12, it is for example screwed into place.

As soon as the inner tube 14 is filled with blood up to the lower or rearward end 14" then the blood extraction process is terminated and the inner tube 14, which is axially slidably guided in the cover bore 10 through end wall 20 is drawn axially out of the sample tube 12. When the cover 20 is fixedly connected with the inner tube 14. The inner tube is removed at and together with the cover 20. The partial vacuum which arises in the lower part of the sample tubule 12 after closing of the vent passage 21 thereby sucks the blood column 15 out of the inner tube 14 into the sample tubule 12.

In the embodiment of FIGS. 3, 3a and 3b the cover 20 is sealingly screwed by means of the inner thread 3 provided on its axially projecting collar 20" and on an external thread 4 provided on the upper end of the sample tubule 12. The right-cylindrical inner tube 14 is axially sealingly guided through the central axial bore 10 of the cover 20 and an abutment 7 provided in this region restricts the insertion depth of the inner tube 14 into the sample tubule 12 in the manner which can be seen from FIG. 3.

In contrast to the preceding embodiments the inner tube 14 projects somewhat further beyond the cover 20 where, in the still cylindrical region a roughened or knurled surface 9 is provided at which the inner tube 14 can be grasped in force transmitting manner by the operator for the purpose of removing it.

In accordance with FIGS. 3, 3a and 3b the outer wall of the inner tube 14 is flattened in the region of the cover bore 10 in such a way that a lateral, axially directed, vent passage 13" is formed, which is in particular evident from FIGS. 3a and 3b, with this passage extending above and below the cover. A plug 6 is non-losably connected to the cover 20 via a flexible band 5 which can be formed in one piece with the cover 20. By means of this plug the cover bore 10 can be sealingly closed after the inner tube has been removed.

The manner of operation of the embodiment of FIGS. 3, 3a and 3b is as follows:

Prior to blood extraction the inner tube 14 is pushed into the cover bore 10 of the cover 20 screwed onto the sample tubule 12 until the abutment 7 contacts the cover 20, which has been from above. In this state the vent passage 13" provides a vent connection between the interior of the sample tubule 12 and the surrounding atmosphere.

In this state blood 15 can be taken, which gradually spreads out in the inner tube 14 as a column 15 in similar manner to the preceding embodiments, with the diameter of the inner tube 14 and its length being so sized that the blood column 15 does not break away and can move continuously downwardly in the manner of a column, even in the vertical position of FIG. 3. The operator can readily observe the filling process as a result of the transparent construction of the sample tubule 12 and of the inner tube 14, and can interrupt the taking of blood on achieving the desired degree of filling. As soon as the cannula 11 has been removed from the vein 16 the operator can grasp the inner tube 14 in the roughened region 9 above the cover 20 and pull the tube 14 out upwardly, with the vent passage 13" first being closed in that its lower boundary (1 in FIG. 3a) enters into the region of the cover bore 10 from where on the entire circumference of the inner tube 14 sealingly contacts the edge of the cover bore 10. A vacuum is now generated in the interior of the sample tube 12 by further drawing out of the inner tube 14 and as a result of this vacuum the blood column 15 passes out of the lower end 14" of the inner tube 14 and into the interior of the sample tubule 12. Air can be sucked in from the atmosphere through the cannula 11, in just the same way as in other embodiments.

The inner tube 14 is preferably drawn fully out of the cover 20 and is for example thrown away, whereupon, the interior of the sample tubule 12 can be hermetically closed relative to the outside, for example for the purpose of despatch of the sample tubule 12, by means of the plug 6 which is sealingly inserted from above into the cover bore 10.

In later use in the laboratory the cover 20 is then unscrewed whereby the interior of the sample tube 12 becomes accessible.

The blood extraction device of the invention is expedient for taking up 100 to 1000 μl, with the preferred quantity range lying between 500 and 700 μl.

The receiving capacity of the inner tube 14 is thus substantially larger than that of a capillarly which in general only accommodates 20 to 50 μl and which at most accommodates 100 μl.

The cannula 11 which is used should be as thin as possible so that the filling of the inner tube 14 takes place as slowly as possible and in a manner which can be readily surveyed.

The determining factors for the filling speed of the inner tube 14 are, on the one hand, the venous pressure which cannot be influenced by the user and, on the other hand, the ratio between the inner cross-section of the cannula 11 and the inner cross-section of the inner tube 14. This ratio should lie between 1:5 and 1:15, in particular at 1:10. Preferred absolute values for the internal diameter of the cannula are 0.2 to 0.3, in particular 0.25 mm and for the internal diameter of the inner tube 14, 2 to 5, in particular 3 to 4 and preferably approximately 3.5 mm.

The diameter of the inner tube must be so selected taking account of the diameter of the cannula and the venous pressure that the speed of flow into the internal tube is so reduced that the filling process can be acurately observed and timely interrupted.

The cover 20 can be pushed onto the sample tubule 12, can be snapped onto it, or can be screwed onto it.

I claim:

1. A blood extraction device comprising a sample tubule (12) which is hermetically sealed at its rear end, a cannula (11), a front end (11') of which can be inserted into the vein (16) of a patient, an inner tube (14) extending into the interior of the sample tubule (12) and sealingly adjoining a rear end (11") of the cannula (11), so that the rear end (11") of the cannula (11) is in flow communication with the interior of the sample tubule (12), a front end of the sample tubule (12) being closed and including an air vent (13, 13', 13", 23);

the inner tube (14) having an internal cross-section which is greater than an internal cross-section of the cannula (11) and sufficiently small so that during the taking of blood a continuous blood column (15) flows from the rear end (11") of the cannula (11) into the inner tube (14) while being retained inside the inner tube in all positions of the sample tubule (12) relative to the direction of gravity at least for as long as the cannula (11) is inserted into the vein (16);

the inner tube (14) further extending into a region of the sample tubule (12) at the rear end thereof; and a cover (20) mounted on the front of the sample tubule (12), the inner tube (14) passing centrally through a bore (10) in the cover, an end of the inner tube proximate the cannula carrying a mounting element (17) projecting forwardly beyond the cover (20), and a rear end of the inner tube (14) extending to the vicinity of the rear end of the sample tubule (12).

2. An apparatus in accordance with claim 1, wherein the air vent (13, 13', 13") is provided in the cover (20).

3. An apparatus in accordance with claim 1, wherein the inner tube (14) has an internal cross-section which is of a size such that when the cannula (11) is withdrawn from the vein (16), or is disconnected from the inner tube (14), and when the blood sample tubule (12) is in an upright position, the blood column (15) which has collected in the inner tube (14) automatically emerges downwardly into the sample tubule (12).

4. An apparatus in accordance with claim 3, wherein the inner tube (14) projects into the sample tubule (12) so that, after the blood column (15) in the inner tube has been transferred to the sample tubule (12), the blood level (19) in the sample tubule is located beneath a lower end (18) of the inner tube (14).

5. An apparatus in accordance with claim 1, including means for generating a partial vacuum in the interior of the sample tube after filling the inner tube (14) with the blood column (15) so that the blood column (15) is sucked out of the inner tube (14) into the sample tubule.

6. An apparatus in accordance with claim 5, including a cover (20), and wherein the inner tube (14) is fixedly connected to the cover (20) and sealingly passes through it.

7. An apparatus in accordance with claim 6, characterized in that the cover (20) includes a collar (20') acting as a cylinder, cooperates in the manner of a piston-in-cylinder arrangement with the sample tubule (12), has a peripheral bead (12') which acts as a piston, and includes at least one vent passage (13) in the inner wall of the collar (20') bridging a sealing surface of the peripheral bead (12') in the blood extraction position.

8. An apparatus in accordance with claim 6, including a ring piston (22) at the front end of the sample tubule (12) on the inside thereof in sealing connection with an outer wall of the inner tube (14), and a vent passage (13') in the outer wall of the inner tube (14) bridging an inner sealing surface of the ring piston (22) in the blood extraction position.

9. An apparatus in accordance with claim 6, including a piston (14') arranged at an end of the inner tube (14) corresponding to the hermetically sealed end of the sample tubule and in sealing contact with an inner wall of the sample tubule (12), and including at least one vent passage (21) formed in the inner wall of the sample tubule (12) which bridges a sealing surface of the piston (14') in the blood extraction position only.

10. An apparatus in accordance with claim 9, including an abutment (7) on a part of the inner tube (14) for determining the position of the inner tube (14) in which it is pushed in the sample tubule to the greatest extent.

11. An apparatus in accordance with claim 9, including a plug (6) for closing a bore (10) in the cover.

12. An apparatus in accordance with claim 5, wherein the inner tube (14) is axially displaceable in a bore (10) formed in the cover (20) and has a sufficient length so that it projects outwardly from the cover (20) when the inner tube is pushed in the sample tubule to the greatest extent such that it can be readily grasped.

13. An apparatus in accordance with claim 2 including a vent passage (13'') in the wall of the inner tube (14) connecting the atmosphere with a region immediately adjacent the cover (20) when the inner tube (14) is pushed in the sample tubule to the greatest extent, the vent passage (13'') being arranged so that it is closed for the generation of a partial vacuum even when the inner tube (14) has been slightly withdrawn from the sample tubule to thereby form a sealed sliding connection is between the inner tube (14) and the cover (20).

14. An apparatus in accordance with claim 13, characterized in that the vent passage (13'') is formed by a partial flattening (8) of the inner tube (14) which extends past the cover (20) in the state in which the inner tube (14) is pushed in the sample tubule to the greatest extent.

15. An apparatus in accordance with claim 1, wherein the inner tube (14) has a length selected such that when it is pushed into the tubule to the maximum extent possible an end of the inner tube (14) in the region of the rear end of the sample tubule is spaced from the rear end of sample tube (12).

16. An apparatus in accordance with claim 1, wherein the inner tube (14) and the sample tubule (12) are transparent.

17. An apparatus in accordance with claim 1, wherein at least one of the inner tube and the sample tubule is translucent.

* * * * *